United States Patent [19]
Tynan, III

[11] Patent Number: 5,399,675
[45] Date of Patent: Mar. 21, 1995

[54] ACIDIC POLYCYCLIC ETHER ANTIBIOTICS AND MICROORGANISMS USEFUL IN THE PRODUCTION THEREOF

[75] Inventor: Edward J. Tynan, III, Gales Ferry, Conn.

[73] Assignee: Pfizer Inc., New York, N.Y.

[21] Appl. No.: 772,374

[22] PCT Filed: Jun. 1, 1989

[86] PCT No.: PCT/US89/02400
§ 371 Date: Nov. 5, 1991
§ 102(e) Date: Nov. 5, 1991

[87] PCT Pub. No.: WO90/15062
PCT Pub. Date: Dec. 13, 1990

[51] Int. Cl.$^6$ ............ C07H 17/04; A61K 31/70; C12P 19/00
[52] U.S. Cl. .................. 536/16.8; 514/27; 435/101; 435/119; 435/252.1; 536/18.7; 426/658
[58] Field of Search ............ 435/75, 119, 169, 170, 435/172.1; 536/16.8; 514/27; 549/330, 343

[56] References Cited

U.S. PATENT DOCUMENTS

| | | | |
|---|---|---|---|
| 4,148,882 | 4/1979 | Celmer et al. | 424/122 |
| 4,407,946 | 10/1983 | Labeda et al. | 435/75 |
| 4,746,650 | 5/1988 | Cullen et al. | 514/27 |
| 4,804,680 | 2/1989 | Goudie et al. | 514/460 |

FOREIGN PATENT DOCUMENTS

| | | |
|---|---|---|
| 0169011 | 7/1985 | European Pat. Off. |
| 0255335 | 7/1987 | European Pat. Off. |
| 314330 | 5/1989 | European Pat. Off. |
| 0400915 | 5/1990 | European Pat. Off. |
| 2186787 | 8/1981 | Japan |
| 60-130394 | 7/1985 | Japan |

OTHER PUBLICATIONS

Westley, Adv. Appl. Microbiol. 22:177 (1977).
Harris, D. L. et al., Vet. Med/SAC 67:61–64 (1972).
Leng in "Physiology of Digestion and Metabolism in the Ruminant," Phillipson et al., Eds., Oriel Press, Newcastle-upon-Tyne, England, 1970, pp. 408–410.
McCullough in "Feedstuffs," Jun. 19, 1971, p. 19.
Church et al. in "Digestive Physiology and Nutrition of Ruminants", vol. 2, 1971, pp. 622 and 625.
"The Merck Veterinary Manual," Siegmund et al., Eds., Merck & Co., Rahway, N.J., 5th Ed., pp. 431–433 (1979).
Stanbury et al., Principles of Fermentation Technology, 1984, Pergamon Press, pp. 55–59.

*Primary Examiner*—John W. Rollins
*Assistant Examiner*—Howard C. Lee
*Attorney, Agent, or Firm*—Peter C. Richardson; Gregg C. Benson; James T. Jones

[57] ABSTRACT

This invention relates to novel acidic polycyclic ether antibiotics CP-91,243 and CP-91,244 of the formula

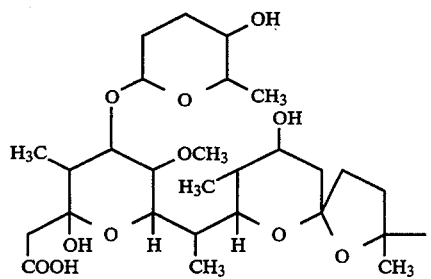

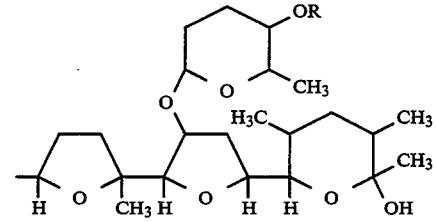

wherein R is H in CP-91,243 and R is CH$_3$ in CP-91,244. The invention also relates to novel *Actinomadura roseorufa* microorganisms; processes for producing the novel antibiotics and the known antibiotic UK-58,852; methods for controlling coccidial infections in poultry, enteritis in livestock and swine dysentery; methods for promoting growth and/or improving efficiency of feed utilization in ruminant or monogastric animals; and nutrient feed compositions.

3 Claims, No Drawings

ACIDIC POLYCYCLIC ETHER ANTIBIOTICS AND MICROORGANISMS USEFUL IN THE PRODUCTION THEREOF

This is a National filing under 35 U.S.C. 371 based on PCT/US89/02400 filed Jun. 1, 1989.

TECHNICAL FIELD

This invention relates to novel acidic polycyclic ether antibiotics and the pharmaceutically acceptable cationic salts thereof. This invention also relates to novel *Actinomadura roseorufa* microorganisms. Further, this invention relates to processes for producing the novel acidic polycyclic ether antibiotics and the known acidic polycyclic ether antibiotic UK-58,852. Further still, this invention relates to methods for controlling coccidial infections in poultry, enteritis in livestock and swine dysentery by administering the novel antibiotics of this invention to said animals. This invention also relates to nutrient feed compositions comprising the novel antibiotics of this invention and to methods for promoting growth and/or improving efficiency of feed utilization in ruminant or monogastric animals by administering the novel antibiotics of this invention.

BACKGROUND ART

Acidic polycyclic ether antibotics are a class of compounds characterized by their effects on cation transport in mitochondria. This family of antibiotics includes such well known agents as monensin; nigericin; grisorixin; dianemycin; salinomycin; mutalomycin; ionomycin and leuseramycin. The subject has been reviewed by Westley, "Polyether Antibiotics", Adv. Appl. Microbiol., 22,177, 1977.

The polycyclic ether antibiotics listed immediately above are active against Gram-positive bacteria, fungi and protozoa. In particular those antibiotics exhibit potent anti-coccidial activity. They therefore have been employed with varying degrees of success in the treatment of a variety of animal infections.

The well-known protozoan disease, coccidiosis, continues to be a serious problem and its control is of economic importance to veterinary science, especially to the poultry industry. Coccidiosis results from infection by one or more species of Eimeria or Isospora (for a summary, see Lund and Farr in "Diseases of Poultry," 5th ed., Biester and Schwarte, Eds., Iowa State University Press, Ames, Ia., 1965, pp. 1056-1096). There are six species of coccidia which produce easily discernible morbidity in susceptible chickens. *Eimeria tenella, E. necatrix, E. brunetti, E. acervulina, E. maxima* and *E. mivati* produce damage either directly through destruction of epithelial cells of the digestive tract or indirectly through production of toxins. Three other species of protozoa belonging to the same genus are considered to be relatively innocuous; however, *E. mitis, E. hagani* and *E. praecox* are capable of reducing weight gain, lowering feed efficiency and adversely affecting egg production.

In view of the great economic losses due to coccidiosis and the known disadvantages of existing anti-coccidial agents, the search for better anti-coccidial agents continues.

Enteritis is another disease which can cause severe economic losses to livestock producers. Enteritis occurs in chickens, swine, cattle and sheep and is attributed mainly to anaerobic bacteria, particularly *Clostridium perfringens* and viruses. Enterotoxemia in ruminants, an example of which is "overeating disease" in sheep, is a condition caused by *C. perfringens* infection.

Swine dysentery is one of the most common swine diseases diagnosed in the United States. Additionally, the disease is prevalent in many other countries and annually causes considerable losses in stock to swine growers around the world. It has recently been discovered that a large spirochete is the causative organism of the disease. This organism, *Treponema hyodysenteriae*, has now been isolated and shown to be capable of producing the disease [Harris, D. L. et al. "Swine-Dysentery-1, Inoculation of Pigs with Treponema hyodysenteriae (New species) and Reproduction of the Disease," Vet Med/SAC, 67, 61–64, 1972]. It must be noted that it is not known whether *T. hyodysenteriae* is the sole causative organism of swine dysentery. From the data available, however, it can be concluded that it is a primary source of the infection.

Performance enhancement (increased rate of growth and/or increased efficiency of feed utilization) in ruminants such as cattle, and in monogastric animals such as swine, is another economically desirable objective of veterinary science. Of particular interest is improved performance achieved by increasing the efficiency of feed-utilization. The mechanism for utilization of the major nutritive portion of ruminant feeds is well known. Microorganisms in the rumen of the animal degrade carbohydrates to produce monosaccharides and then convert these monosaccharides to pyruvate compounds. Pyruvates are metabolized by microbiological processes to form acetates, butyrates or propionates, collectively known as volatile fatty acids. For a more detailed discussion, see Leng in "Physiology of Digestion and Metabolism in the Ruminant," Phillipson et al., Eds., Oriel Press, Newcastle-upon-Tyne, England, 1970, pp. 408–410.

The relative efficiency of volatile fatty acid utilization is discussed by McCullough in "Feedstuffs" Jun. 19, 1971, p. 19; Eskeland et al. in J. An. Sci., 33, 282, 1971; and Church et al. in "Digestive Physiology and Nutrition of Ruminants", Vol 2, 1971 pp. 622 and 625. Although acetates and butyrates are utilized, propionates are utilized with greater efficiency. Furthermore, when too little propionate is available, animals may develop ketosis. A beneficial compound, therefore, stimulates animals to produce a higher proportion of propionates from carbohydrates, thereby increasing carbohydrate utilization efficiency and also reducing the incidence of ketosis.

Yet another disease which causes economic losses to live-stock producers is caused by the protozoan parasite *Theileria parva*. That disease, theileriosis, is also known as "East Coast fever", "Coastal fever" or "Rhodesian tick fever". The Theileria parasite invades but does not destroy red blood cells which gives rise to acute or chronic febrile infections. In cattle the disease is characterized by high fever, swelling of the lymph nodes, emaciation and high mortality. The disease is a very serious problem in East and Central Africa. See further "The Merck Veterinary Manual", Siegmund et al., Eds., Merck & Co., Rahway, N.J., 5th Ed., pp. 431–433 (1979).

U.S. Pat. No. 4,746,650 discloses the production of UK-58,852 by cultivation of *Actinomadura roseorufa* Huang Sp. nov., ATCC 39697 in an aqueous nutrient medium under submerged aerobic conditions. UK- 58,852 is disclosed therein as a novel acidic polycyclic ether antibiotic of the formula

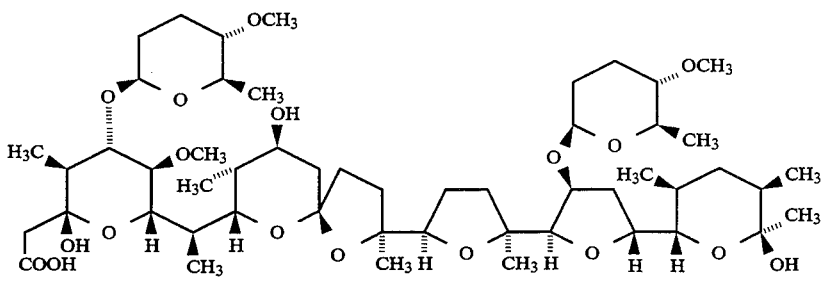

(I)

Also produced in the fermentation of said *Actinomadura roseorufa* Huang sp. nov., ATCC 39697, are two related, minor components, each of which is antibiotically effective in controlling coccidiosis. The two minor components are of the formula (II), below, wherein R is H and $R^1$ is $CH_3$; and R and $R^1$ are both $CH_3$, respectively

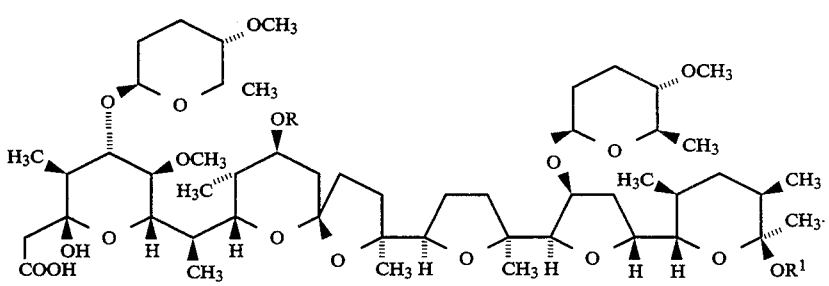

(II)

DISCLOSURE OF THE INVENTION

This invention concerns two novel acidic polycyclic ether antibiotics, designated CP-91,243 and CP-91,244 herein, having the formula

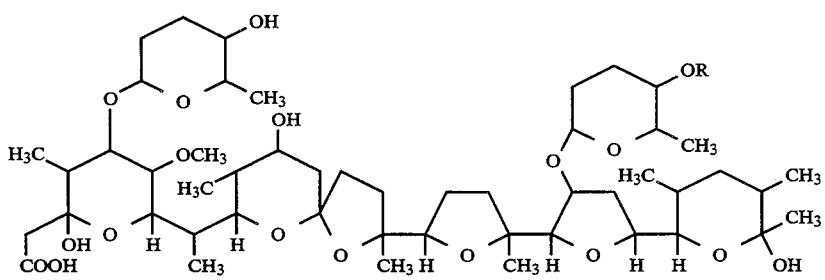

(III)

wherein R is H for antibiotic CP-91,243 and R is $CH_3$ for antibiotic CP-91,244. Also included within the scope of this invention are the pharmaceutically-acceptable cationic salts of said antibiotics.

Further, this invention relates to certain novel microorganisms which are mutants obtained from *Actinomadura roseorufa* having the identifying characteristics of ATCC 53666. The novel microorganisms of this invention are capable of producing, by cultivation, CP-91,243 and/or CP-91,244. Two such novel microorganisms are *Actinomadura roseorufa* having the identifying characteristics of ATCC 53869 and ATCC 53870. This invention also concerns further mutants, transformants and recombinants of said novel microorganisms which are capable of producing, by cultivation, CP-91,243 and/or CP-91,244. Further still, this invention concerns novel microorganisms which are mutants obtained from *Actinomadura roseorufa* having the identifying characteristics of ATCC 53666 and further mutants, transformants and recombinants thereof all of which, in addition to producing CP-91,243 and/or CP-91,244 upon cultivation, also produce UK-58,852. Still, further this invention relates to processes for producing CP-91,243, CP-91,244 and the known acidic polycyclic ether antibiotic UK-58,852 by cultivation of the novel microorganisms of this invention. This invention also concerns methods for controlling coccidial infections in poultry, enteritis in livestock such as chickens, swine, cattle and sheep and swine dysentery by administering CP-91,243 and/or CP-91,244 alone or in combination with UK-58,852 to said animal. Also within the scope of this invention are methods for promoting growth and/or feed utilization in ruminants and monogastric animals which comprise administering to said animals CP-91,243 and/or CP-21,244 individually or in combination with each other and/or UK-58,852. Further still, this invention is directed to nutrient feed compositions which comprise CP-91,243 and/or CP-91,244 alone or in combination with UK-58,852.

The term "*Actinomadura roseorufa* having the identifying characteristics of . . . " as used herein and in the appendant claims shall include the actual ATCC deposited culture to which such term refers as well as any other microorganisms of *Actinomadura roseorufa* which have the same identifying characteristics as the deposited culture referred to by such term.

DETAILED DESCRIPTION

The novel acidic polycyclic ether antibiotics CP-91,243 and CP-91,244 are produced by microorganisms obtained by the mutation of a strain of *Actinomadura roseorufa* Huang sp. nov. having the identifying characteristics of ATCC 53666 as described below. *Actinomadura roseorufa* ATCC 53666 has been deposited under the terms of the Budapest Treaty in the American Type Culture Collection, Rockville, Md. in connection with applicant's pending U.S. patent application Ser. No. 113,563, filed Oct. 26, 1987 and assigned to the assignee hereof. All restrictions on the availability to the public of the microorganism will be irrevocably removed upon granting of a patent thereon. N-methyl-N'-nitro-N-nitrosoguanidine (NTG) was used as the mutagen. Single colonies of the treated microorganism were then examined for their production profile. The general procedure comprised growing ATCC 53666 in an aqueous nutrient medium under submerged aerobic conditions with shaking at a temperature of 28° C. The choice of medium for the growth study is not critical.

A suitable medium consists of cerelose (10.0 g), corn starch (5.0 g), corn steep liquor (5.0 g), N-Z Amine YTT (5.0 g), (Registered Trademark for enzymatic digest of casein, Humko Sheffield Chemical Co. Inc.), and cobalt chloride (0,002 g) which is suspended in one liter of water, pH adjusted to 7.0 with sodium hydroxide and dispensed (800 ml) to a Fernbach flask. After sterilization by autoclaving, flasks are inoculated with a slant growth suspension or frozen vegetative mycelia, then incubated with agitation on a shaker at about 200 rev/min and a temperature of 28° C. for seven to eight days. A 50 ml aliquot is then removed and the mycelia homogenized by a Teflon pestle tissue grinder followed by ultrasonic fragmentation. The fragmented mycelia then were centrifuged, washed free of medium, resuspended in 50 ml of fresh medium in a 300 ml Erlenmeyer flask, and incubated by shaking at 32° C. for two hours. Then, the cells were again centrifuged, washed free of medium and suspended in 50 ml of tris(hydroxymethyl)-aminomethane-malate buffer, pH 9.0. Aliquots of this suspension were treated with NTG at concentrations of 750 mcg/ml to 1500 mcg/ml for one hour on a rotary water bath shaker at 250 to 300 rev/min. and a temperature of 34° C. After treatment, the cells were centrifuged, washed free of mutagen and aliquots were serially diluted, plated onto a solid nutrient medium and the plates incubated at 28° C. until the colony forming units were of sufficient size for transferring to slants. A suitable medium for plates and slants is ATCC Medium No. 172 with N-Z Amine Type A (Humko Sheffield Chemical Co. Inc.) decreased to 1.0 g/l The inoculated slants were allowed to grow at 28° C. for 10 to 14 days after which time they were ready for testing. This was done by inoculating 300 ml Erlenmeyer flasks containing 25 ml of a suitable medium (one such medium contains cerelose, 45.0 g; soy flour 10.0 g; corn steep liquor, 15.0 g; $MnSO_4.H_2O$, 0.1 g; $MgSO_4.7H_2O$, 0.1 g; Cobalt chloride, 0.002 g; and calcium carbonate, 3.0 q; one liter of water and the pH of the medium is adjusted to 7.0). After sterilization by autoclaving for 30 minutes at 121° C., the flasks were inoculated with individual slant growth suspensions and incubated by shaking at 28° C. on a rotary shaker for 7 days. Mutant cultures were detected by examining methylisobutyl ketone extracts of harvested whole broths after spraying developed thin-layer chromatographic plates (silica gel) with vanillin reagent and heating at 100° C. for five minutes. The developing system was composed of 9 parts chloroform to 1 part methanol which gave Rf values of about 0.2 for CP-91,243, about 0.4 for CP-91,244 and about 0.7 for UK-58,852. Two mutant cultures were thus obtained which produce CP-91,243, CP-91,244 and UK-58,852. Those mutants are identified in the culture collection of Pfizer Inc. as FD 28455 and FD 28518. The morphological and cultural characteristics of the thus-obtained mutants are substantially those described for *A. roseorufa* ATCC 53666. The distinguishing characteristic of these mutants is their ability to produce a mixture of CP-91,243 and CP-91,244.

Cultivation of the mutants and isolation of antibiotics CP-91,243 and CP-91,244 may be conducted under conditions similar to those employed in previous fermentations yielding polycyclic ether antibiotics. See, for example, U.S. Pat. No. 4,361,649. Cultivation preferably takes place in aqueous nutrient media under preferably submerged aerobic conditions with agitation at a temperature of 24° C. to 36° C. Nutrient media useful for cultivation include a source of assimilable carbon such as sugars, starches and glycerol; a source of organic nitrogen such as casein, enzymatic digest of casein, soybean meal, cotton seed meal, peanut meal, wheat gluten, soy flour, blood meal, meat meal and fish meal. A source of growth substances such as grain solubles, fish meal, cotton seed meal and yeast extract as well as mineral salts such as sodium chloride and calcium carbonate and trace elements such as iron, magnesium, copper, zinc, cobalt and manganese may also be utilized with advantageous results. If excessive foaming is encountered during fermentation, antifoam agents such as vegetable oils or silicones may be added to the fermentation medium. Aeration of the medium in vessels for submerged growth is preferably maintained at the rate of $\frac{1}{2}$ to 2 volumes of sterile air per volume of fermentation broth per minute forced into the broth through a sparger. Agitation may be maintained by means of agitators generally familar to those skilled in the fermentation art. The rate of agitation depends on the type of agitator employed. A shake flask is usually run at 150 to 300 cycles per minute whereas a fermenter is usually run at 300 to 1700 revolutions per minute. Asceptic conditions must, of course, be maintained through the transfer of the organism and throughout its growth.

Inoculum for preparation of the antibiotics according to this invention may be obtained by employing growth from a slant of the desired microorganism culture of this invention or Roux bottles inoculated with said culture or a thawed mycelia suspension of said culture. A solid medium suitable for initial growth of the microorganism on slants and Roux bottles is ATCC medium No. 172. The liquid medium previously mentioned in the mutational study is suitable to prepare the vegetative mycelia prior to freezing. The resultant growth may be used to inoculate either shake flasks or inoculum vessels or the inoculum vessels may be seeded from the shake flasks. Maximum growth in shaken flasks is usually reached in 4 to 8 days, whereas inoculum in submerged inoculum vessels will usually be in the most favorable period in 4 to 5 days.

The progress of the antibiotic production during fermentation can be monitored qualitatively by thin-layer chromatography after visualization by spraying with vanillin reagent as previously described or the developed plate can also be overlayed with brain heart infusion agar seeded with Bacillus subtilis and incubated at 37° C. for 16 hours to visualize the antibiotics. Thin-layer chromatography is also a useful tool for analyzing the composition of crude and purified materials extracted from the fermentation broth.

The antibiotics CP-91,243, CP-91,244 and UK-58,852 produced by the fermentation of said mutants accumulate in the mycelium and in the broth and can be separated and recovered by extracting the harvested whole unfiltered fermentation broth, i.e., the whole broth, with an organic solvent such as chloroform, ethyl acetate, methylisobutyl ketone or butanol at the naturally prevailing pH. Alternatively, to avoid serious emulsion problems the mycelium is separated and both it and the clarified broth are extracted individually with an organic solvent. The solvent extracts are concentrated to a thin syrup and pure CP-91,243, CP-91,244 and UK-58,852 obtained by column chromatography.

A typical method of separation and recovery of the antibiotics of this invention is as follows: The whole broth from the fermentation of the mutant was extracted with methylisobutyl ketone. Evaporation of the extract in vacuo gave a reddish oil which was poured onto a column of silica gel. The silica gel column was then eluted with chloroform/methanol (19:1) and the eluates examined by thin-layer chromatography. Fractions enriched in CP-91,243, CP-91,244 and UK-58,852 were combined and concentrated or evaporated to dryness. Each antibiotic containing fraction which had been evaporated to dryness was then dissolved in ethyl acetate and those fractions were poured onto individual silica gel columns. The silica gel columns were then eluted with ethyl acetate and again eluates examined by thin-layer chromatography. Fractions containing CP-91,243 and CP-91,244 were crystallized from ethyl acetate while UK-58,852 was crystallized from the hexane.

The antibiotics of this invention can be recovered from the fermentation in association with the mycelium by evaporation of the whole broth by known methods, including spray drying, or by separation of the mycelium from the broth by filtration or centrifugation. The mycelial products thus obtain comprise the antibiotics on the surface of the mycelium and in the interstices thereof rendering the mycelium a useful carrier.

The mutants identified in the culture collection of Pfizer Inc. as FD 28455 and FD 28518 have been deposited under the terms of the Budapest Treaty in the American Type Culture Collection, Rockville, Md., a recognized depository affording permanence of the deposits and ready accessibility thereto by the public if a patent is granted on this application. Culture FD 28455 has been given the designation *Actinomadura reseorufa* ATCC 53869. Culture FD 28518 has been given the designation *Actinomadura roseorufa* ATCC 53870. The deposits are available during pendency of this application to one determined by the Commissioner of the United States Patent and Trademark Office to be entitled thereto under 37 C.F.R. 1.14 and 35 U.S.C. 122, and in accordance with foreign patent laws in countries wherein counterparts of this application, or its progeny, are filed. All restrictions on the availability to the public of the microorganism deposited will be irrevocably removed upon granting of a patent thereon.

The cultural characteristics of *Actinomadura roseorufa* ATCC 53869 and ATCC 53870 are substantially the same as those of *Actinomadura roseorufa* 53666 with the exception that ATCC 53869 and ATCC 53870 additionally produce CP-91,243 and CP-91,244.

Taxonomic investigations of *Actinomadura roseorufa* ATCC 53666 were carried out by L. H. Huang who provided the following descriptions.

The culture was planted from a slant into ATCC no. 172 broth and grown for four days at 28° C. on a shaker. It was then centrifuged for 20 minutes, washed three times with sterile distilled water and planted on media commonly used for identification of members of the Actinomycetales.

The culture was incubated at 28° C. and the results were read at varying times but most commonly were taken at 14 days. The colors are described in common terminology, but exact colors were determined by comparisons with color chips from the *Color Harmony Manual*, Fourth edition. The method of whole-cell amino acid analysis is that described in Becker et al., *Appl. Microbiol.*, 12, 421–423, 1964. Whole-cell sugars were analyzed by the methods described in Lechevalier, *J. Lab. Clin. Med.*, 71, 934–944, 1968; and in Staneck and Roberts, *Appl. Microbiol.* 28, 226–231, 1974. For the purpose of comparison, the type culture of *Actinomadura roseorufa* ATCC 39,697 was used.

Identification media used for the characterization of the cultures and references for their composition are as follows:

1. Tryptone-Yeast Extract Broth —(ISP #1 medium, Difco).
2. Yeast Extract-Malt Extract Agar —(ISP #2 medium, Difco).
3. Oatmeal Agar —(ISP #3 medium, Difco).
4. Inorganic Salts-Starch Agar —(ISP #4 medium, Difco).
5. Glycerol-Asparagine Agar —(ISP #5 medium, Difco).
6. Peptone-Yeast Extract Iron Agar —(ISP #6 medium, Difco).
7. Czapek-Sucrose Agar —S. A. Waksman, The Actinomycetes, Vol. 2, medium no. 1, p. 328, 1961.
8. Glucose-Asparagine Agar —Ibid, medium no. 2, p. 328.
9. Bennett's Agar —Ibid, medium no. 30, p. 331.
10. Emerson's Agar —Ibid, medium no. 28, p. 331.
11. Nutrient Agar —Ibid, medium no. 14, p. 330.
12. Gordon and Smith's Tyrosine Agar —R. E. Gordon and M. M. Smith, *J. Bacteriol.* 69: 147–150, 1955.
13. Casein Agar —Ibid.
14. Calcium Malate Agar —S. A. Waksman, *Bacteriol. Rev.* 21: 1–29, 1957.
15. Gelatin —R. E. Gordon and J. M. Mihm, *J. Bacteriol.* 73: 15–27, 1957.
16. Starch —Ibid.
17. Organic Nitrate Broth —Ibid.
18. Dextrose Nitrate Broth —S. A. Waksman, The Actinomycetes, Vol. 2, medium no. 1, p. 328, 1961, with 3 g dextrose substituted for 30 g sucrose and agar omitted.
19. Potato Carrot Agar —M. P. Lechevalier, *J. Lab. and Clinical Med.* 71: 934–944, 1968, but use only 30 g potatoes, 2.5 g carrots and 20 g agar.
20. 2% Tap Water Agar.
21. Gauze's #1 Mineral Agar —G. F. Gauze et al., Problems in the Classification of Antagtonistic Actinomycetes, English Ed., p. 13, 1957.
22. Gauze's #2 Organic Agar —Ibid.
23. Skim Milk —Difco.
24. Cellulose utilization — a) H. L. Jensen, Proc. Linn. Soc. N.S.W. 55: 231-248, 1930.
b) M. Levine and H. W. Schoenlein, A Compilation of Culture Media, medium no. 2511, 1930.

25. Utilization of Organic Acids —R. E. Gordon et al., Int. J. Syst. Bacteriol. 24: 54-63, 1974.
26. Acid Production from carbohydrates —Ibid.
27. Hydrolysis of Hippurate and Esculin —Ibid.
28. Decomposition of Adenine, Hypoxanthine, Xanthine, and Urea —Ibid.
29. Resistance to Lysozyme —Ibid.
30. Carbohydrate Utilization —C-2 Medium, H. Nonomura and Y. Ohara, J. Ferment. Technol. 49: 887-894, 1971.
31. Temperature Range —ATCC medium 172 in ATCC Culture Collection Catalogue, 15th ed., p. 608, 1982.

A description of culture *Actinomadura roseorufa* ATCC 53666

Yeast Extract-Malt Extract Agar —Growth good, pink-red to red (6 ½ia, 7ia, 6ia), raised, wrinkled, with white aerial mycelium; reverse red (7ia); no soluble pigment.

Oatmeal Agar —Growth moderate, cream (2ca), slightly raised, smooth, or appearing as isolated colonies; aerial mycelium none to sparse, white; reverse cream (2ca); no soluble pigment.

Inorganic Salts-Starch Agar —Growth poor to moderate, colorless to cream (2ca), thin, smooth; aerial mycelium none to sparse, white; reverse same as surface; no soluble pigment.

Glycerol-Asparagine Agar —Growth poor to moderate, cream (2ca), with pink to red dots (6ea, 6½ga); aerial mycelium none to sparse, white; reverse colorless to cream (2ca), with red dots; no soluble pigment.

Czapek-Sucrose Agar —Growth poor to moderate, cream (2ca), with pink to red dots (5ca, 6½ia); aerial mycelium none to sparse, white; reverse colorless to cream (2ca); no soluble pigment.

Glucose-Asparagine Agar —Growth moderate to good, pink to red (6½ga, 6½na), raised; smooth, granular to wrinkled; aerial mycelium white to pale pink (6ea); reverse red (6½ga, 6½ia); soluble pigment pale yellowish (3ca).

Gordon and Smith's Tyrosine Agar —Growth moderate to good, pink-orange (5ea), moderately raised, wrinkled; aerial mycelium none to sparse, white; reverse same as surface; soluble pigment yellowish (2lc).

Calcium Malate Agar —Growth scant, colorless, thin, smooth, no aerial mycelium; reverse colorless; no soluble pigment.

Casein Agar —Growth moderate to good, pink-orange to orange (4ia, 5ia), moderately raised, wrinkled, no aerial mycelium; reverse yellowish to pale pink (3ga, 5ea); with brown (3lc) soluble pigment.

Bennett's Agar —Growth good, red to dark red (6½ne, 6½ng), raised, wrinkled; aerial mycelium white to pink (6ea); reverse red (6 ½lc); with brown (3ne) soluble pigment.

Emerson's Agar —Growth good to excellent, orange (5la, 5na), raised, wrinkled, with white aerial mycelium; reverse orange (5ic); no soluble pigment.

Nutrient Agar - Growth moderate, pale orange (5ea, 5ga), slightly raised, smooth, or appearing as isolated colonies, no aerial mycelium; reverse pale orange (5ga); no soluble pigment.

Gelatin Agar Growth moderate to good, pale orange (4ga), moderately raised, smooth to wrinkled; aerial mycelium sparse, white; reverse pale orange (4ga); no soluble pigment.

Starch Agar —Growth moderate to good, pale orange (5ga), moderately raised, smooth to wrinkled; aerial mycelium sparse, white; reverse same as surface; no soluble pigment.

Potato Carrot Agar —Growth poor to moderate, cream to pale pink (2ca, 4ca), thin to slightly raised; aerial mycelium sparse, white; reverse cream to pale pink (4ca); no soluble pigment.

Tap Water Agar —Growth poor, colorless to cream (1½ca), thin, smooth; aerial mycelium sparse, white; reverse same as surface; no soluble pigment.

Gauze's Mineral Medium 1 —Growth moderate, pink to red (5ca, 6la), with red dots (6lc), slightly raised, smooth; aerial mycelium none to sparse, white; reverse same as surface; no soluble pigment.

Gauze's Organic Medium 2 —Growth moderate to good, pink-orange (5ga), moderately raised, slightly wrinkled; aerial mycelium sparse, white; reverse same as surface; no soluble pigment.

Morphological Properties —After seven weeks of incubation, no spores were found on any of the media used. On potato carrot agar, however, hyphal swellings were produced terminally, laterally or intercalarily; and were single and smooth. They were globose, oval to elliptical, and measured 1.2-2.5 m diam. or 1.2-2.2 ×0.9-1.8 m. The similar structures were also found on yeast extract-malt extract agar, oatmeal agar, tap water agar, gelatin agar, Czapek-sucrose agar, and Gauze's mineral medium 1.

Biochemical Properties —Melanin not produced; hydrogen sulfide not produced; gelatin liquefied; starch not hydrolyzed; nitrate reduced to nitrite; slight growth on Jensen's cellulose broth but no growth on Levine and Schoenlein's cellulose broth; no disintegration on both cellulose broths; coagulation and peptonization on milk; digestion of calcium malage negative; tyrosine digestion positive; casein digestion positive.

Carbohydrate utilization: glucose, rhamnose, and sucrose utilized; arabinose, fructose, inositol, mannitol, raffinose, and xylose not utilized.

The positive tests included: utilization of acetate, propionate, and pyruvate; acid production from glucose, rhamnose, maltose, and trehalose.

The following tests were negative: decomposition of adenine, xanthine, hypoxanthine, and urea; hydrolysis of esculin and hippurate; resistance to lysozyme; utilization of benzoate, citrate, dextrin, lactate, malate, mucate, oxalate, phenol, and succinate; acid production from arabinose, fructose, inositol, mannitol, raffinose, sucrose, xylose, adonitol, cellobiose, dulcitol, erythritol, galactose, glycerol, lactose, mannose, melezitose, malibiose, alpha-methyl-D-glucoside, ribose, salicin, sorbitol, sorbose, and starch.

Whole-cell Analysis —The whole-cell hydrolysates contain mesodiaminopimelic acid, galactose, glucose, madurose, ribose, and rhamnose.

| Temperature Relations - | | | |
| --- | --- | --- | --- |
| 21° C. | 28° C. | 37° C. | 45° C. |
| Moderate Growth | Good Growth | Moderate Growth | No Growth |

*Actinomadura roseorufa* ATCC 53666 is characterized by the inability to produce melanin; the pink, pink-orange, orange to red substrate mycelium; and the presence of meso-diaminopimelic acid and madurose as whole-cell components. Despite a long incubation period of up to seven weeks, the culture failed to produce spores although hyphal swellings were produced on some media.

*Actinomadura roseorufa* ATCC 53666 was similar to *Actinomadura roseorufa* Huang ATCC 39,697 (see European Patent Application 169 001) in most of the cultural characteristics and almost all of the biochemical properties. On gelatin agar and starch agar, colonies of ATCC 53666 were pale orange rather than pale cream. On tyrosine agar and Emerson's agar, they showed some tint of orange rather than brown. ATCC 53666, unlike *A. roseorufa,* coagulated milk. These differences were minor and hence culture ATCC 53666 is considered as a new strain of *A. roseorufa.*

Also within the scope of this invention are further mutants, transformants and recombinants of mutants of the microorganism *Actinomadura roseorufa* which microorganism has the identifying characteristics of ATCC 53666 and which mutants of said microorganism include those having the identifying characteristics of ATCC 53869 or ATCC 53870. Such further mutants can occur spontaneously or be induced via methods well known to those skilled in the art. Similarly, transformants and recombinants of the microorganisms can be obtained through a variety of classical and biotechnological techniques well known to those skilled in the art. All such further mutants, transformants and recombinants are within the scope of this invention provided they produce either or both of the antibiotics CP-91,243 and CP-91,244. Also, within the scope of this invention are said further mutants, transformants and recombinants which, in addition to producing antibiotics CP-91,243 and/or CP-91,244, also produce UK-58,852 upon cultivation.

The novel acidic polycyclic ether antibiotics of this invention are tested for in vitro antibacterial activity by standard methods in which the minimum inhibitory concentrations (MIC's) in mcg/ml against one or more microorganisms is measured. One such procedure is the one recommended by the International Collaborative Study on Antibiotic Sensitivity Testing (Ericcson and Sherris, *Acta. Pathologica et Microbiologia Scandinav,* Supp. 217, Section B: 64–68 [1971]), and employs brain heart infusion (BHI) agar and an inocula replicating device. Overnight growth tubes are diluted 100 fold for use as the standard inoculum (20,000–100,000 cells in approximately 0.002 ml are placed on the agar surface; 20 ml of BHI agar/dish). Twelve 2 fold dilutions of the test compound are employed, with initial concentration of the test drug being 200 mcg/ml. Single colonies are disregarded when reading plates after 18 hours at 37° C. The susceptibility (MIC) of the test organism is accepted as the lowest concentration of compound capable of producing complete inhibition of growth as judged by the naked eye.

Efficacy data for CP-91,243, CP-91,244 and their salts against coccidial infections in chickens is obtained by the following method. Groups of 3 ten-day old pathogen free white leghorn cockerel chicks are fed a mash diet containing the compound under study or its sodium and/or potassium salt uniformly dispersed therein. After being on this ration for 24 hours each chick is inoculated per os with oocysts of the particular species of Eimeria being tested. Other groups of 3 ten-day old chicks are fed a similar mash diet without the subject compound or its salts. They are also infected after 24 hours and serve as infected controls. Yet another group of 3 ten-day old chicks are fed the same mash diet without antibiotic and are not infected with coccidia. These served as normal controls. The results of treatment are evaluated after six days.

The criteria used to measure anticoccidial activity consists of lesion scores of 0 to 4 after J. E. Lynch, "A New Method of the Primary Evaluation of Anticoccidial Activity", *Am. J. Vet. Res.,* 22, 324–326, 1961. Activity is measured by dividing the lesion score of each treated group by the lesion score of the infected control.

The value of animal feeds has generally been determined directly by feeding the animal. British Patent Specification No. 1,197,826 details an in vitro rumen technique whereby the changes occurring in feeds brought about by microorganisms are measured more readily and with great accuracy in the evaluation of animal feeds. This technique involves the use of an apparatus in which the digestive processes of the animals are conducted and studied in vitro. The animal feeds, rumen inoculum and various growth promotants are introduced into and withdrawn from a laboratory unit under carefully controlled conditions and the changes taken place are studied critically and progressively during the consumption of the feed by the microorganisms. An increase in the propionic acid content of the rumen fluid indicates that a desirable response in overall ruminant performance has been brought about by the growth promotant in the feed composition. The change in propionic acid content is expressed as percent of the propionic acid content found in the control rumen fluid. Long term in vivo feeding studies are used to show a reliable correlation between propionic acid increase in the rumen fluid and improved animal performance.

Rumen fluid is collected from a fistulated cow which is fed on a commercial fattening ration plus hay. The rumen fluid is immediately filtered through cheese cloth, and 10 ml added to a 50 ml conical flask containing 400 mg of standard substrate (68% corn starch+17% cellulose+15% extracted soybean meal), 10 ml of a pH 6.8 buffer and the test compound. The flasks are gassed with oxygen free nitrogen for about two minutes, and incubated in a shaking water bath at 39° C. for about 16 hours. All tests are conducted in triplicate.

After incubation, 5 ml of the sample is mixed with 1 ml of 25% metaphosphoric acid. After 10 minutes 0.25 ml of formic acid is added and the mixture centrifuged at 1500 rpm for 10 minutes. Samples are then analyzed by gas-liquid chromatography by the method of D. W. Kellog, J. Dairy Science, 52, 1690, 1969. Peak heights for acetic, propionic and butyric acids are determined for samples from untreated and treated incubation flasks.

For use in the treatment of coccidiosis in poultry, enteritis in livestock such as chickens, swine, cattle and sheep and swine dysentery, the compounds of this invention are administered orally in a suitable carrier. Conveniently, the medication is simply carried in the drinking water or in the poultry feed, so that a therapeutic dosage of the agent is ingested with the daily water or poultry ration. The agent can be directly metered into drinking water, preferably in the form of a liquid, water-soluble concentrate (such as aqueous solution of a water soluble salt) or added directly to the feed, as such, or in the form of a premix or concentrate. A premix or concentrate of therapeutic agent in a carrier is commonly employed for the inclusion of the agent in the feed. Suitable carriers are liquid or solid, as desired, such as water, various meals; for example, soybean oil meal, linseed oil meal, corncob meal, and mineral mixes such as are commonly employed in poultry feeds. A particularly effective carrier is the respective animal feed itself; that is, a small portion of such feed. Further, the mycelium can be used as the carrier. The carrier facilitates uniform distribution of the active materials in the finished feed with which the premix is blended. This is important because only small proportions of the present potent agents are required. It is important that the compound be thoroughly blended into the premix and, subsequently, the feed. In this respect, the agent may be dispersed or dissolved in a suitable oily vehicle such as soybean oil, corn oil, cottonseed oil, and the like, or in a volatile organic solvent and then blended with the carrier. It will be appreciated that the proportions of active material in the concentrate are capable of wide variation since the amount of agent in the finished feed may be adjusted by blending the appropriate proportion of premix with the feed to obtain a desired level of therapeutic agent.

High potency concentrates may be blended by the feed manufacturer with proteinaceous carrier such as soybean oil meal and other meals, as described above, to produce concentrated supplements which are suitable for direct feeding to animals. In such instances, the animals are permitted to consume the usual diet. Alternatively, such concentrated supplements may be added directly to the feed to produce a nutritionally balanced, finished feed containing a therapeutically effective level of the compound of this invention. The mixtures are thoroughly blended by standard procedures, such as in a twin shell blender, to ensure homogeneity.

It will, of course, be obvious to those skilled in the art that the use levels of the compound described herein will vary under different circumstances. For example, in the treatment of coccidiosis in poultry, low-level medication, during the growing period; that is, during the first 6 to 12 weeks for chickens, is an effective prophylactic measure. In the treatment of established infections, higher levels may be necessary to overcome the infection. The use level in feed will generally be in the range of 15 to 120 ppm. When administered in drinking water, the level which will be that which will provide the same daily dose of medication, i.e., 15 to 120 ppm, factored by the weight ratio of the average daily consumption of feed to the average daily consumption of water.

The antibiotics of this invention can be administered as the free acid or as cationic salts thereof. For example, the sodium or potassium salts of the antibiotics can be employed. Such salts are formed by methods well known to those skilled in the art. Antibiotics CP-91,243 and CP-91,244 can be administered individually or in combination with each other and/or UK-58,852. The antibiotics-CP-91,243, CP-91,244 and UK-58,852 can be used in the crude form or as dried fermentation broth containing the antibiotics at the desired potency concentrations.

The present invention is illustrated by the following examples. However, it should be understood that the invention is not limited to the specific details of these examples.

EXAMPLE 1

Fermentation of Actinomadura roseorufa FD 28455 (ATCC 53869) and Recovery of Antibiotics

A. Preparation of Inoculum

A sterile aqueous medium having the following composition was prepared.

| Ingredient | Grams/Liter |
| --- | --- |
| Cerelose | 10.0 |
| Corn Starch | 5.0 |
| Corn Steep Liquor | 5.0 |
| NZ Amine YTT* | 5.0 |
| Cobalt Chloride | 0.002 |

*(Registered trademark for enzymatic digest of casein, Humko Sheffield Chemical Co. Inc.)

After the pH was adjusted to 7.0, the medium was dispensed (800 ml) into 2800 ml Fernbach flasks, cotton plugged/paper capped and sterilized by autoclaving for 60 minutes at 121° C. (15 p.s.i.). After cooling, the medium was inoculated with a vegetative cell suspension from a slant of FD 28455. The flasks were shaken at 28° C. on a rotary shaker having a displacement of 1½ to 2½ inches and 150 to 200 cycles per minute for 6 days.

B. Fermentation and Isolation of CP-91,243, CP-91,244 and UK-58,852

A Fernbach flask containing 800 ml of the grown culture was used to inoculate a 14-liter fermentation vessel containing 8 liters of sterile medium of the following composition to which 4 ml of silicone antifoaming agent had been added:

| Ingredient | Grams/Liter |
| --- | --- |
| Cerelose | 55.0 |
| Soy Flour | 10.0 |
| Corn Steep Liquor | 15.0 |
| Blood Meal | 10.0 |
| $MnSO_4.H_2O$ | 0.1 |
| $MgSO_4.7H_2O$ | 0.1 |
| $CoCl_2.6H_2O$ | 0.002 |
| Calcium Carbonate | 3.0 | pH adjusted to 6.9–7.0

Fermentation was carried out at 30° C. with stirring at 500 revolutions per minute and aeration at 0.75 volume air per volume broth per minute until substantial activity was produced. The CP-91,243/CP-91,244/UK-58,852 in the broth and recovery streams were visualized by using silica gel thin-layer chromatography plates developed with a system consisting of 9:1 chloroform:methanol. The plates were sprayed with vanillin reagent (6 g vanillin in 100 ml ethanol and 3% concentrated $H_2SO_4$) and heated at 100° C. for 5 minutes. The antibiotics appear as reddish-blue spots. Alternatively, the plate was overlayed with agar seeded with B. subtilis, to which 0.4 ml of a 5% solution of 2,3,5-triphenyl-2H-tetrazolium chloride had been added, and incubated at 37° C. for 16 hours to visualize the antibiotics as colorless areas against a red background.

The whole broth (15 liters) obtained by combining the fermentation broths of two 14 liter fermenters was stirred for 20 minutes with an equal volume of methylisobutyl ketone. The aqueous and solvent phases were separated, the aqueous phase was discarded and the solvent was concentrated to an oil (24 g). This concentrate was chromatographed on a column of 700 g of silica gel (70-230 mesh, Universal Absorbents) in a 5.5 cm ×8 cm glass column using chloroform:methanol (19:1) as the eluate. The flow rate was 10 ml/min and one fraction was taken per minute. These fractions were examined by thin-layer chromatography (Analtech silica Gel GF plates), developed in a system of chloroform:methanol (9:1) and visualized by spraying/heating with vanillin reagent as described above. Those fractions containing mostly CP-91,243, CP-91,244 or UK-58,852 were combined by antibiotic and concentrated to yield 0.7 g CP-91,243, 4.9 g CP-91,244 and 3.6 g UK-58,852.

The concentrate containing CP-91,244 was chromatographed again on a column of 200 g silica gel (70-230 mesh, Universal Adsorbents) in a 2.5 cm×100 cm glass column using ethyl acetate as the eluate. The flow was 10 ml/min and one fraction taken per minute. The fractions were examined by thin-layer chromatography as described above and the fractions enriched in CP-91,244 were combined, concentrated and crystallized from ethyl acetate to yield 850 mgs of CP-91,244.

The CP-91,243 and UK-58,852 fractions were chromatographed in the same manner to yield 280 mg CP-91,243 which crystallized from ethyl acetate and 1.5 g UK-58,852 which was crystallized from hexane.

Structural assignments for CP-91,243 and CP-91,244 then were made based upon C-13NMR, elemental analysis and FAB/MS of the sodium salts of the antibiotics in comparison to known antibiotics UK-58,852 and UK-61,689.

CP-91,243 gave the following: mp 178°-180° C., $[\alpha]_D^{25} = -7.6°$ (c=1, CH$_3$OH) and FAB/MS 996 (M+Na)$^+$; Anal. Calc'd for C$_{50}$H$_{83}$O$_{18}$NaH$_2$O: C, 59.22; H, 8.47 Found: C, 59.22; H, 8.23.

C-13 nmr [chemical shift (ppm) in CDCl$_3$ (with two drops CD$_3$OD) with number of hydrogens in parentheses]: 179.3 (0), 107.6(0), 103.3(1), 102.5(1), 98.0(0), 97.0(0), 87.1(1), 84.8(0), 84.3(0), 82.6 (1), 82.4(1), 81.8(1), 81.0(1), 80.2(1), 76.0(1), 75.8(1), 73.4(1), 71.4(1), 70.9(1), 70.2(1), 67.9(1), 67.6(1), 59.6(3), 45.4(2), 44.7(1), 39.9(1), 39.0(2), 36.6(2), 33.8(1), 33.8(2), 33.5(1), 33.5(2), 33.1(1), 32.5(2), 32.5(2), 32.3(2), 32.3(2), 31.4(2), 31.0(2), 27.5(3), 26.9(2), 26.1(3), 23.2 (3), 18.1 (3), 17.9 (3), 17.4 (3), 16.8 (3), 12.3(3), 10.9(3) and 10.3(3).

CP-91,244 gave the following: mp 154°-157° C., $[\alpha]_D^{25} -4.8°$ (c=1, CH$_3$OH) and FAB/MS 1010 (M+Na)$^+$; Anal. Calc'd for C$_{51}$H$_{85}$O$_{18}$Na:C, 60.65; H, 8.59 Found: C, 60.41; H, 8.58.

C-13 nmr [chemical shift (ppm) in CDCl$_3$ with number of hydrogens in parentheses ]: 179.3 (0), 107.6(0), 103.2(1), 102.5(1), 98.0(0), 97.0(0), 87.1(1), 84.7(0), 84.3(0), 82.6(1), 82.4(1), 81.8(1), 80.9(1), 80.3(1), 80.0(1), 75.8(1), 74.7(1), 73.1(1), 71.7(1), 70.2(1), 67.8(1), 67.5(1), 59.6(3), 56.8(3), 45.7 (2), 44.8(1), 40.0(1), 39.0(2), 36.6(2), 33.9(2), 33.7 (1), 33.6(1) 33.6(2), 33.2(1), 32.6(2), 32.4(2), 31.7 (2), 31.5(2), 30.7(2), 27.7(3), 27.0(2), 26.9(2), 26.1 (3), 23.3(3), 18.4(3), 18.1(3), 17.5(3) , 17.0(3), 12.4 (3), 11.1 (3) and 10.4 (3).

Thus, CP-91,243 and CP-91,244 were assigned the structural formula

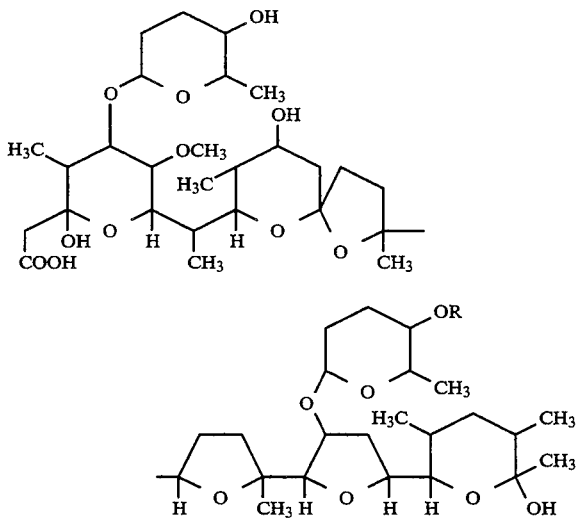

wherein R is H in CP-91,243 and R is CH$_3$ in CP-91,244.

EXAMPLE 2

Fermentation of *Actinomadura roseorufa* FD 28518 (ATCC 53870) and Recovery of Antibiotics Following the procedure described in Example 1, *Actinomadura roseorufa* ATCC 53870 was fermented, the broth (15 liters) was extracted and the solvent phase was concentrated to an oil (17 g). The concentrate was chromatographed according to the procedure described in Example 1. Those fractions containing mostly CP-91,243, CP-91,244 or UK-58,852 were combined by antibiotic and concentrated to yield 5 g CP-91,243, 3.5 g CP-91,244 and 2.5 g UK-58,852. The concentrates were further chromatographed and crystallized according to the procedure described in Example 1 for the concentrates therein to yield 1.2 g CP-91,243, 480 mg CP-91,244 and 190 mg UK-58,852.

What is claimed is:

1. An antibiotic of the formula

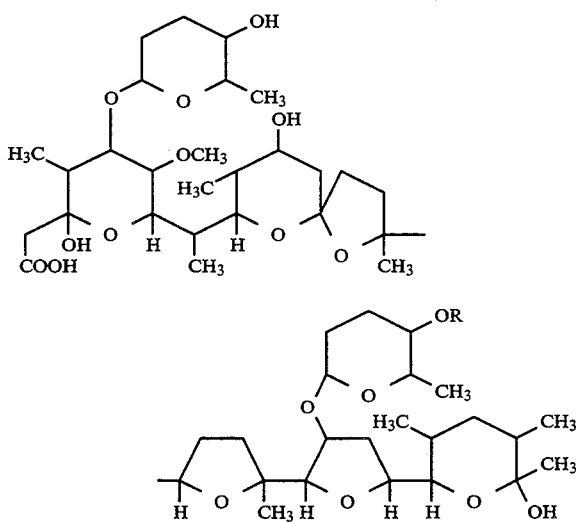

and the pharmaceutically-acceptable cationic salts thereof wherein R is H or CH$_3$.

2. The antibiotic according to claim 1 wherein R is H.

3. The antibiotic according to claim 1 wherein R is CH$_3$.